United States Patent [19]
Slavicek et al.

[11] Patent Number: 5,882,913
[45] Date of Patent: Mar. 16, 1999

[54] STRAIN OF GYPSY MOTH VIRUS WITH ENHANCED POLYHEDRA AND BUDDED VIRUS PRODUCTION

[75] Inventors: James M. Slavicek, Dublin; Nancy Hayes-Plazolles, Deleware, both of Ohio

[73] Assignee: The United States of American as represented by the Secretary of Agriculture, Washington, D.C.

[21] Appl. No.: 908,215

[22] Filed: Aug. 7, 1997

[51] Int. Cl.$^6$ .................................. C12N 5/00; C12N 7/00
[52] U.S. Cl. ........................ 435/235.1; 435/325; 424/93.6
[58] Field of Search ................................ 435/235.1, 325; 424/93.6

[56] References Cited

U.S. PATENT DOCUMENTS

| | | |
|---|---|---|
| 3,876,772 | 4/1975 | Biel et al. . |
| 4,911,913 | 3/1990 | Hostetter et al. . |
| 4,945,057 | 7/1990 | Temeyer et al. . |
| 5,132,220 | 7/1992 | Shapiro et al. . |
| 5,180,581 | 1/1993 | Miller et al. . |
| 5,244,805 | 9/1993 | Miller . |
| 5,266,317 | 11/1993 | Tomalski et al. . |
| 5,352,451 | 10/1994 | Miller et al. . |
| 5,420,031 | 5/1995 | Slavicek et al. . |
| 5,462,732 | 10/1995 | Slavicek et al. . |

FOREIGN PATENT DOCUMENTS

WO 90/10387  9/1990  WIPO .

OTHER PUBLICATIONS

Burand, John P., et al., "Alternation of *Autographa californica* Nuclear Polyhedrosis Virus DNA upon Serial Passage in Cell Culture," *Virology*, 119:223–229 (1982).

Cusack, T., et al., Effect of Serial Passage on Genetic Homogeneity of a Plaque Variant of *Lymantria dispar* Nuclear Polyhedrosis Virus (Hamden LDP–67), *J. gen. Virol*, 70:2963–2972(1989).

Fraser, M.J., et al., "Acquisition of Host Cell DNA Sequences by Baculoviruses: Relationship Between Host DNA Insertions and FP Mutants of *Autographa californica* and *Galleria mellonella* Nuclear Polyhedrosis Viruses," *Journal of Virology*, 47(2):287–300 (Aug. 1983).

Lynn, Dwight E., "Enhanced Infectivity of Occluded Virions of the Gypsy Moth Nuclear Polyhedrosis Virus for Cell Cultures," *Journal of Invertebrate Pathology*, 63:268–274 (1994).

Podgwaite, John D., et al., "Effects of Aerially Applied Gypchek on Gypsy Moth (Lepidoptera: Lymantriidae) Populations in Maryland Woodlots," *Journal of Economic Entomology*, 85(4):1136–1139 (Aug. 1992).

Slavicek, James M., "Analysis of Viral Genomic Heterogeneity in the *Lymantria Dispar* Nuclear Polyhedrosis Virus Formulation Gypchek," *International Symposium on Applications of Biotechnology to Tree Cultur, Protection and Utilization*, Columbus, Ohio, Aug. 5–8, 1991.

Slavicek, James M., "Enhancement of *Lymantria Dispar* Nuclear Polyhedrosis Virus Efficacy, Potency, and Polyhedra Production in Cell Culture Through Biotechnology," *Proceedings of the Annual Gypsy Moth Conference*, Nov. 4–7, 1991.

Slavicek, James M., et al., "Properties of Two *Lymantria dispar* Nuclear Polyhedrosis Virus Isolates Obtained from the Microbial Pesticide Gypchek," *Journal of Invertebrate Pathology*, 59:142–148 (1992).

*Primary Examiner*—Leon B. Lankford, Jr.
*Attorney, Agent, or Firm*—Janet I. Stockhausen; M. Howard Silverstein; John D. Fado

[57] ABSTRACT

An isolate of the gypsy moth virus *Lymantria dispar* nuclear polyhedrosis virus (LdNPV) that is characterized by enhanced polyhedra production, enhanced budded virus production, and stable polyhedra production during serial passage in cell culture is disclosed. The isolate, designated LdNPV 122b, has been deposited at the American Tissue Culture Collection and has been assigned number ATCC VR2577. Also disclosed is a viral insecticide having an insecticidally effective amount of polyhedra produced in cell culture. A method for protecting plants from insects against which LdNPV is toxic is disclosed.

20 Claims, 5 Drawing Sheets

Fig. 1A

Polyhedra Production per flask by LdMNPV Isolates ± SD

| Virus:Cell Infection Ratio | A21-15 | 122b | Level of Significant Difference Between A21-15 and 122b Values |
|---|---|---|---|
| 1:1 | $1.2 \times 10^8 \pm 5.3 \times 10^6$ | $2.5 \times 10^8 \pm 2.6 \times 10^7$ | $P < 0.05$ |
| 1:5 | $1.5 \times 10^8 \pm 6.9 \times 10^6$ | $2.9 \times 10^8 \pm 4.3 \times 10^7$ | $P < 0.05$ |
| 1:10 | $1.1 \times 10^8 \pm 1.4 \times 10^7$ | $3.7 \times 10^8 \pm 5.5 \times 10^7$ | $P < 0.05$ |
| 1:50 | $8.3 \times 10^7 \pm 9.8 \times 10^6$ | $3.5 \times 10^8 \pm 3.7 \times 10^7$ | $P < 0.05$ |
| 1:100 | $3.8 \times 10^7 \pm 1.4 \times 10^7$ | $1.7 \times 10^8 \pm 2.0 \times 10^7$ | $P < 0.05$ |
| 1:500 | $2.1 \times 10^7 \pm 5.3 \times 10^6$ | $1.6 \times 10^8 \pm 4.3 \times 10^7$ | $P < 0.05$ |
| 1:1000 | $1.5 \times 10^7 \pm 1.5 \times 10^6$ | $9.3 \times 10^7 \pm 5.2 \times 10^7$ | $P < 0.05$ |

Budded Virus Production by LdMNPV Isolates + SD

| Viral Isolate | TCID/$_{50}$ per ml | Means followed by the same letter do not differ significantly at $P < 0.05$ based on LSD |
|---|---|---|
| 122b | $3.3 \times 10^7 \pm 1.5 \times 10^7$ | a |
| A21-MPV | $4.2 \times 10^6 \pm 1.6 \times 10^6$ | b |
| A21-2 | $2.6 \times 10^7 \pm 9.3 \times 10^6$ | a |
| B21-1 | $2.1 \times 10^7 \pm 9.7 \times 10^6$ | a |
| 122-2 | $1.5 \times 10^7 \pm 2.1 \times 10^6$ | a |
| 163-2 | $2.1 \times 10^7 \pm 5.7 \times 10^6$ | a |
| 5-6 | $2.7 \times 10^7 \pm 2.5 \times 10^6$ | a |

FIG. 2B

STRAIN OF GYPSY MOTH VIRUS WITH ENHANCED POLYHEDRA AND BUDDED VIRUS PRODUCTION

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The gypsy moth, *Lymantria dispar*, is a particularly troublesome tree defoliator. Since its import into the United States in 1869 for use in the production of silk fibers in Massachusetts, the gypsy moth has caused major tree infestations. The gypsy moth has spread throughout New England, New York, Delaware, Maryland, New Jersey, Pennsylvania, Virginia, West Virginia, Ohio, Michigan, North Carolina, and Wisconsin. (McFadden, et al., *Forest Insect Guilds: Patterns of Interaction with Host Trees*, Y. N. Baranchikov, et al., pp. 172–186, U.S. Department of Agriculture, For. Serv. Gen. Tech. Rep. NE-153, Radnor, Pa., 1989; Blackburn, et al. *Proceedings of the Annual Gypsy Moth Review*, pp. 261–351, 1994).

Several chemical pesticides have been used in the control of gypsy moth infestations. DDT is one of the most effective chemical insecticides in controlling gypsy moths. However, DDT and other chemical insecticides have been found to adversely affect the environment in myriad ways. Broad spectrum insecticides such as DDT are not only effective in exterminating unwanted pests; these chemicals also kill insects that we consider beneficial. Destruction of insect species results in disruptions to the entire ecosystem. For control of gypsy moth infestations, DDT use has been abandoned in favor of a less harmful chemical, diflubenzeron, and the biorational agent *Bacillus thuringiensis* (Bt).

A growing awareness that forestry and agricultural practices have a great impact on the environment has spawned research directed toward the development of biological insect control agents as an alternative to the use of chemical pesticides. Insect baculoviruses have received considerable attention as promising agents for the biological control of insects. These viruses have been isolated from hundreds of insect species, have a narrow host range, can be formulated for aerial application, and can be manipulated through genetic engineering to enhance viral efficacy. Insect baculoviruses have essentially no adverse environmental impact.

Baculoviruses, such as the *Lymantria dispar* nuclear polyhedrosis virus (LdNPV), have two distinct morphological forms which serve different roles in the process of infection (Blissard and Rohrmann, *Annu. Rev. Entomol.*, 35:127–155, 1990). The infection cycle begins with larval ingestion of a polyhedron, a polyhedral shaped crystalline protein matrix that contains viral particles. The polyhedron is dissolved within the insect midgut, thereby releasing the occluded virus particles, which in turn infect the insect. Early after infection, a budded (nonoccluded) form of virus is produced in infected cells. Budded virions cause a systemic infection of the insect larval host. Late in infection, virions that are produced become occluded into polyhedra.

A gypsy moth virus, LdNPV, has been used on a limited basis as a gypsy moth control agent. One advantage of LdNPV is that it is specific for the gypsy moth. Consequently, LdNPV is the agent of choice for gypsy moth control, particularly in environmentally sensitive areas. However, control of gypsy moth by LdNPV has not been fully exploited due to high production costs and low efficacy.

There is currently no commercial production of LdNPV. LdNPV is produced in limited amounts by the Forest Service and the Animal and Plant Health Inspection Service in gypsy moth larvae. Production in larvae is expensive; currently, the cost of generating enough virus to treat an acre of forest with the viral insecticide is several times higher than treatment with diflubenzeron or Bt.

Production of LdNPV in cell culture is a less expensive alternative to production in larvae. The virus may be propagated in cell culture using the *L. dispar* 652Y (Ld652Y) ovarian cell line. However, propagation of nuclear polyhedrosis viruses in cell culture generally yields low numbers of polyhedra, the protein-encapsulated form of the virus that is most suitable for use as an insecticide. Nuclear polyhedrosis viruses tend to mutate to a form that produces few polyhedra upon serial transfer, a process that is necessary during scale-up of cell cultures. Baculovirus few polyhedra (FP) mutants arise at a high frequency during serial passage in cell culture. In contrast to wild-type or many polyhedra (MP) virus, FP mutants produce few polyhedra, and those that are produced are essentially noninfectious. Lack of potency is probably due to a reduced number of viral particles found in the polyhedra of FP mutants (Hink and Strauss, *J. Invertebr. Pathol.*, 27:49–55, 1976; Potter, et al., *J. Virol.*, 18:1040–1050, 1976; Fraser and Hink, *Virology*, 177:366–378, 1982; Slavicek et al., *Biol. Con.*, 5:251–261, 1995). FP mutants also synthesize greater numbers of budded virus than wild-type virus. Increased production of budded virus results in the conversion of the virus population from one exhibiting an MP phenotype to one with an FP phenotype during serial passage in cell culture. FP mutants have been identified in the *Autographa californica* MNPV (Hink and Strauss, *J. Invertebr. Pathol.*, 27:49–55, 1976), *Trichoplusia ni* MNPV (Mackinnon, et al., *J. Ultrastruc. Res.*, 49:419–435, 1974; Potter, et al., *J. Virol.*, 18:1040–1050, 1976), *Galleria mellonella* MNPV (Fraser and Hink, *Virology* 177:366–378, 1982), and LdNPV (Slavicek, et al., *J. Invertebr. Pathol.*, 59:142–148, 1992; Slavicek, et al., *Biol. Con.* 5:251–261, 1995). Because the efficacy of a viral insecticide is a function of the concentration of infective viral particles, the formation of mutants that produce fewer polyhedra (FP mutants) reduces the efficacy and increases the cost of viral insecticides.

One means by which the efficacy of the viral insecticide may be increased and the per acre cost of viral pest control reduced is by increasing the number of polyhedra produced in cell culture. That may be accomplished by identifying and employing a viral strain that produces large numbers of polyhedra in cell culture, and which does not mutate into the FP form upon serial transfer. U.S. Pat. No. 5,420,031, incorporated by reference herein, discloses a strain of LdNPV (A21-MPV) (ATTC VR2396) that exhibits enhanced polyhedra production stability. This strain has a low frequency of FP mutants relative to wild-type and produces polyhedra at fairly consistent levels. U.S. Pat. No. 5,462,732, incorporated by reference herein, discloses a method for protecting plants from insects against which LdNPV is toxic using ATCC VR2396. Although cells infected with ATCC VR2396 produce higher yields of polyhedra, the viral insecticide continues to be a costly alternative to other, less environmentally friendly, methods of controlling gypsy moth.

In addition to polyhedra yields, other factors that can contribute to the cost of production of viruses in cell culture include the multiplicity of infection needed to achieve infection of the cells and the number of passages that are needed during scale up to large bioreactors. What is needed in the art is a strain of LdNPV that can infect cultured cells at a lower multiplicity of infection, that requires fewer passages, and that produces greater numbers of polyhedra than can be achieved with strains that are known to the art.

BRIEF SUMMARY OF THE INVENTION

The present invention is a gypsy moth virus having the characteristics of ATCC VR2577. These characteristics include the ability to achieve successful infection of cultured cells at a low multiplicity of infection, enhanced polyhedra and budded virus production, and stable polyhedra production during serial passage.

The present invention is also a preparation of a gypsy moth virus designated ATCC VR2577.

The present invention is also an insecticidal composition comprising an insecticidal amount of a gypsy moth virus having the characteristics of ATCC VR2577 and an inert carrier.

The present invention is also a method of protecting plants from insects, comprising applying to an insect or an insect habitat an insecticidally effective amount of a gypsy moth virus having the identifying characteristics of ATCC VR2577.

It is an object of the present invention to provide a LdNPV strain with enhanced polyhedra and budded virus production in cell culture.

It is an object of the present invention to provide a LdNPV strain with stable polyhedra production during serial passage.

It is an object of the present invention to provide a viral strain that is able to predominate over any few polyhedra (FP) mutants that may arise in cultured cells infected with the virus of the present invention.

It is an object of the present invention to provide an insecticidal composition for use in the control of insect pests.

It is an object of the present invention to provide a method for controlling insect pests.

It is an advantage of the present invention that insect control may be provided at lower cost.

Other objects, advantages, and features of the present invention will become apparent after review of the specification, drawings, and claims.

BRIEF DESCRIPTION OF THE SEVERAL VIEWS OF THE DRAWINGS

FIG. 1A is a graph showing the number of polyhedra produced in Ld652Y cells infected with LdNPV isolates 122$b$ or A21-15 as a function of the multiplicity of infection. FIG. 1B is a tabular form of the data shown in FIG. 1A.

FIG. 2A is a graphical representation of the number of budded virus produced by various LdNPV isolates. FIG. 2B is a tabular form of the data shown in FIG. 2A.

FIG. 3A includes isolates 122$b$, 122-6, 122-7, and 122-8; FIG. 3B includes isolates 122$b$, B21-12, B21-13, and B21-14; FIG. 3C includes isolates 122$b$, A21-15, A21-16, and A21-17.

FIG. 4A includes isolates 122$b$, 122-6, 122-7, and 122-8; FIG. 4B includes isolates 122$b$, B21-12, B21-13, and B21-14; FIG. 4C includes 122$b$, A21-15, A21-16, and A21-17.

DETAILED DESCRIPTION OF THE INVENTION

Figure 3:
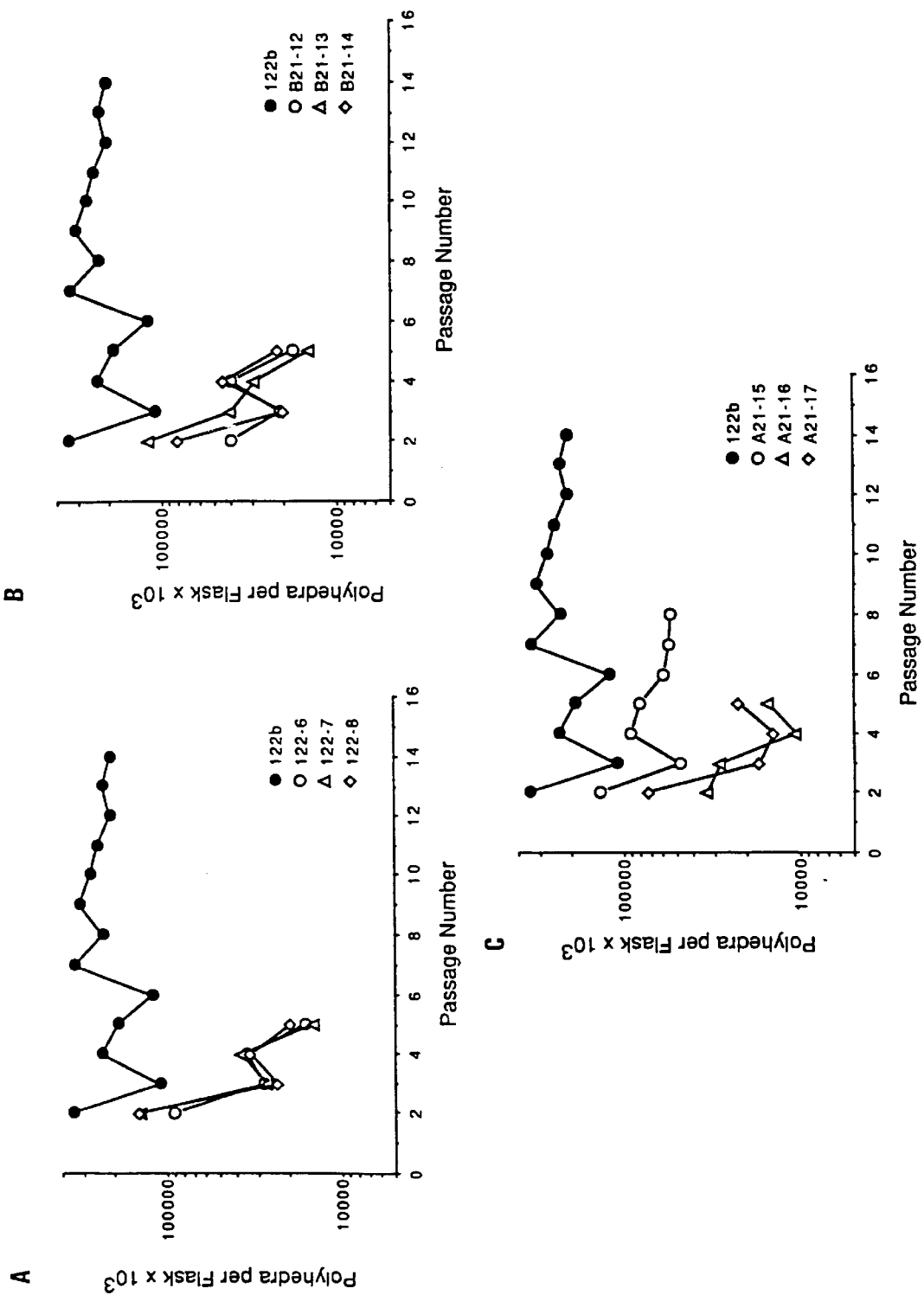
FIG. 3 is a graphical representation of the numbers of polyhedra produced in cells infected with the indicated LdNPV isolates as a function of the number of passages.

One aspect of the present invention is a viral isolate having the characteristics of ATCC VR2577. This virus is characterized by the ability to achieve successful infection of cultured cells at a low multiplicity of infection, enhanced polyhedra and budded virus production, and stable polyhedra production during serial passage. A viral strain that exhibits these characteristics in cell culture would allow commercial scale production of the virus at a lower cost, thereby making the viral insecticide economically attractive.

Virus production in cell culture requires the serial passage of virus from a small bioreactor to successively larger bioreactors. The cost of virus production is in part a function of the number of serial passages necessary to achieve the desired final production volume. Using a viral isolate that produces greater numbers of budded virus reduces the number of passages needed to achieve final production volume, thereby lowering the cost of production. The cost of viral production is also a function of the yield of polyhedra produced in cell culture. Using an isolate that yields higher numbers of polyhedra is another means by which the cost of production can be lowered.

We have identified an LdNPV isolate, designated 122$b$, that has several advantages over wild-type virus. It is able to achieve successful infection of cultured cells at a lower multiplicity of infection than wild-type virus, it exhibits enhanced polyhedra and budded virus production, and it exhibits stable polyhedra production upon serial passage.

The advantageous characteristics of this viral isolate combine to lower the cost of producing a viral insecticide. The higher numbers of polyhedra produced in cells infected with isolate 122$b$ reduces the cost of polyhedra production in cell culture, relative to production in cells infected with the wild-type virus. Because isolate 122$b$ produces more budded virus than wild-type LdNPV, viral infection is spread more readily from cell to cell, fewer serial passages are needed during scale-up of the production process, and the cost of production is reduced. The number of budded virus produced by isolate 122$b$ is comparable to that produced by FP mutants; therefore, FP mutants that arise in cells infected with isolate 122$b$ are unlikely to become the predominant virus type during serial passage. Therefore, polyhedra production is consistent after numerous passages.

The examples below detail the characterization of an isolate having the characteristics of 122$b$. In one embodiment, this isolate is able to produce successful infections at multiplicities of infection (MOI) up to fifty times lower than wild-type. Furthermore, this isolate produces approximately two to four times more polyhedra, and about seven to eight times more budded virus than LdNPV isolate A21-MPV. In addition, this isolate exhibits stable polyhedra production after about 14 serial passages, whereas polyhedra production in cells infected with isolate A21-MPV begins to decrease after about ten serial passages.

The LdNPV isolate 122$b$ was deposited with the American Type Culture Collection, Rockville, Md. on Jun. 10, 1997 at the Accession Number VR2577 under the conditions of the Budapest Treaty. Deposit of this sample does not imply or grant a license to use the virus.

One could obtain a virus having the characteristics of ATCC VR2577 through the American Type Tissue Collection. Alternatively, one could obtain the virus by identifying an LdNPV isolate with the characteristics of ATCC VR2577, i.e., ability to achieve successful infection of cultured cells at a low multiplicity of infection, enhanced polyhedra and budded virus production, and stable polyhedra production during serial passage by the methods described below in the Examples. Preferable starting virus preparations include GYPCHEK, and any strain of LdNPV, preferably wild-type LdNPV strain. Isolate 122b probably arose through a mutation(s) to a wild-type virus strain. Consequently, a virus exhibiting the characteristics of isolate 122b may be isolated from natural populations of LdNPV or from laboratory strains of wild-type virus that are propagated and allowed to mutate.

By "isolate" or "preparation" is meant a virus that has been isolated or purified from its native habitat. The purification may be at any degree that yields a virus preparation capable of characterization as disclosed below.

Partial characterization of genomic DNA revealed no discernable difference between the viral isolate of the present invention and LdNPV isolate 122, the viral isolate from which isolate 122b was derived. Briefly, the genomes of the two viral isolates were examined for restriction fragment length polymorphisms (RFLP) using several Type II restriction enzymes. No genetic heterogeneity was detected by this method. However, it is specifically contemplated that LdNPV isolates having the characteristics of ATCC VR2577 may exhibit genetic heterogeneity detectable by RFLP analysis. It is expected that an LdNPV isolate having the characteristics of ATCC VR2577 and wild-type LdNPV would exhibit genetic heterogeneity detectable by DNA sequence analysis.

The present invention encompasses an LdNPV viral isolate that has been altered through in vitro manipulation of its genome, provided that the virus retains the characteristics of ATCC VR2577.

By "multiplicity of infection" is meant the virus:cell ratio used to establish an infection. A viral isolate with a low multiplicity of infection is one that is able to establish a successful infection in cultured cells at a low virus:cell ratio, relative to wild-type virus. By "low multiplicity of infection" we mean that the viral isolate of the present invention is able to establish successful infections at an MOI five times lower than the MOI at which wild-type virus can establish successful infection. In other embodiments, successful infections may be established using the viral isolate of the present invention at MOIs of 10 times, preferably 25 times, and most preferably 50 times lower than the MOI at which wild-type virus can establish successful infection. By "successful infection" is meant the ability to establish an infection in cell culture that yields at least about $1\times10^8$ polyhedra about 7 days after infecting a T25 flask seeded with about $1\times10^6$ cells.

By "cell culture" is meant cultured cells in which LdNPV can be propagated. The examples below describe the use of the *L. dispar* 652Y ovarian cell line for propagation of LdNPV. However, it is specifically contemplated that the present invention may be practiced using any other suitable host cell that can be grown in cell culture.

Cells infected with a viral isolate having "enhanced polyhedra production" produce polyhedra at significantly higher levels than are produced in cells infected with the wild-type virus. At a high multiplicity of infection, cells infected with a viral isolate having the characteristics of ATCC VR2577 produce polyhedra at levels about 1.9 times greater than cells infected with a wild-type virus. At lower multiplicities of infection, cells infected by a viral isolate having the characteristics of ATCC VR2577 produce polyhedra at levels of 2.5, preferably 3.5, and most preferably 4.5 times greater than levels produced in cells infected with the wild-type virus.

By "enhanced budded virus production" it is meant that significantly more budded virus are produced in cells infected with the isolate than are produced in cells infected with an LdNPV MP isolate, such as A21-MPV. The number of budded virus produced in cells infected with the viral isolate of the present invention may be about 5 to 10, or more, times greater than that produced in cells infected with A21-MPV.

By "stable polyhedra production" it is meant that cells infected with the viral isolate and that have been serially passaged at least ten times continue to produce large numbers of polyhedra. Polyhedra production is assessed by examining infected cells by light microscopy at 100× magnification. Cells in which large numbers of polyhedra are produced appear black in color when visualized by light microscopy. Preferably, cells infected with the viral isolate of the present invention continue to produce large numbers of polyhedra after 10, and most preferably 14, or more serial passages.

The present invention is also an insecticidal composition comprising an insecticidally effective amount of a virus having the characteristics of ATCC VR2577 and an inert carrier. An "insecticidally effective amount" of the virus is defined as that amount of polyhedra that will result in a significant mortality rate of a test group of insect pests, as compared to an untreated group. The insecticidally effective amount may vary with the species of pest, stage of larval development, the nature of the substrate to which the insecticidal composition is applied, the type of vehicle or carrier employed, the period of treatment, temperature and moisture conditions, and other factors. Depending on these various factors, the concentration of virus in the insecticidal composition may vary, but would typically be between $1\times10^8$ to $1\times10^{11}$ polyhedra per liter. Preferably, the concentration of virus would be between $1\times10^{10}$ and $1\times10^{11}$ polyhedra per liter.

One formulation of the insecticidal composition is described in the examples below. It is specifically contemplated that other formulations containing insecticidally effective amounts of the virus would be suitable insecticidal compositions. The present invention encompasses minor variations in the relative amount of the various components in the insecticidal composition. The present invention is intended to include the addition to the composition of agronomically acceptable components known to the art, as well as the substitution of components known to be interchangeable.

It is contemplated that the insecticidal composition could be formulated to include the virus of the present invention in combination with other viruses. For example, the insecticidal composition could contain a virus with the characteristics of ATCC VR2577 and a virus that has insecticidal activity against pests that are not susceptible to the virus of the present invention. In addition, the insecticidal composition could contain the isolate of the present invention as well as another virus that has insecticidal activity against a pest or pests that are susceptible to the insecticidal activity of the present invention.

Any suitable, agronomically acceptable inert carrier known to the art may be used in the practice of the present invention. Examples of suitable carriers include inert solids, such as cellulose or sugars, wettable powders, and aqueous surfactant mixtures.

The present invention is also a method for protecting plants from insects against which LdNPV is toxic. The method comprises the steps of applying to the insects or insect habitat an insecticidally effective amount of a virus having the characteristics of ATCC VP2577. "Insect" includes *Lymantria dispar* and any other species of insect against which LdNPV is toxic. The term "insect" is meant to include any stage in insect development. By "insect habitat" it is meant the location in which the insects are found in the environment.

In the preferred embodiment, the virus may be applied aerially. The virus insecticidal composition described in the examples below is suitable for aerial application, using an appropriately equipped airplane. For example, a 448 kW (600 hp) Grumman AGCAT airplane equipped with 8 atomizers, such as "AU 5000" atomizers manufactured by Micronair has been used for LdNPV application. Delivery of the viral composition could be from $1 \times 10^{11}$ to $5 \times 10^{11}$ polyhedra in 7.5 liters per acre at an airspeed of 160 km/h. (Podgwaite, et al., *J. Economic Entomology*, 85:1136–1139). The present invention is intended to include modes of application other than aerial application.

The nonlimiting examples below are intended to be purely illustrative.

EXAMPLES

Identification and Characterization of a Novel Isolate of LdNPV

The isolate 122b was identified during serial passage of LdNPV isolates in the *Lymantria dispar* 652Y (Ld652Y) ovarian cell line (Goodwin, et al., *In Vitro*, 14:485–494, 1978). The Ld652Y cells were propagated in complete medium containing Goodwin's IPL-52B medium (JRH Biosciences, Lexena, Kans.) with 10% heat-inactivated fetal bovine serum (Hyclone, Logan, Utah) and 6.25 Mm glutamine (Gibco, BRL).

Several different isolates of LdNPV were obtained as follows. Fourth instar gypsy moth larvae were infected per os with isolates A21, B21, 122, and 163 by placing them on diet containing surface-applied polyhedra ($2.5 \times 10^5$ per mm$^2$ of diet surface). At seven days post infection (p.i.), larvae were bled and the hemolymph subjected to centrifugation in an Eppendorf table top centrifuge at 14,000 rpm for 10 minutes to pellet cellular debris. A 100 $\mu$l aliquot of hemolymph was diluted with 9.9 ml of complete medium, and filter sterilized by passing through a series of syringe filters (5, 1.2, and 0.45 $\mu$m). The virus was used to infect $1 \times 10^6$ Ld652Y cells in a T25 flask. Budded virus was harvested seven days p.i., and used to infect $1 \times 10^6$ Ld652Y cells in a T25 flask at a TCID$_{50}$ of 0.2. At seven days p.i. BV was harvested and used to infect cells as described above. The viral isolates were serially passaged in this manner for a total of 5 serial passages. After the fourth serial passage, isolate 122 was plaque purified and a plaque exhibiting a MP phenotype was isolated. This virus was then serially passaged 5 times. After the fifth serial passage the virus plaque purified. Seventeen plaques exhibited a MP phenotype. All 17 plaque purified viral lines were then serially passaged 12 times as described above. After the 12th serial passage, only one viral line, isolate 122b, still exhibited a MP phenotype. All other isolates had mutated to FP mutants.

Determination of the virus:cell ratio that will successfully produce polyhedra

Production of baculoviruses in cell culture bioreactors requires scaling up of the culture volume, which involves the infection of an increasing number of cells contained in bioreactors of successively larger volume. Initially, cells in a relatively low volume (e.g., 1 liter) bioreactor are infected with a virus. The cell culture and virus are incubated for a period of time, and then used to infect cells in a larger volume (e.g., 10 liters) bioreactor. The scaling up process is continued until the desired volume is ultimately reached. Ideally, for commercial uses, cells should be infected with a viral strain that can generate a successful infection at a lower multiplicity of infection, because fewer scale-up steps would be needed. Each scale-up step contributes to higher production cost in terms of media, equipment, and labor costs.

The ability of isolate 122b to generate successful infections at high dilutions was assessed as follows. A series of infections was performed with a fixed number of Ld652Y cells and a decreasing number of viral particles. A second set of infections was conducted using LdNPV A21-15, a wild-type isolate. The virus:cells ratios used were 1:1, 1:5, 1:10, 1:50, 1:100, 1:500, and 1:1000. T25 flasks were seeded with $1 \times 10^6$ Ld652Y cells, and infected with either 122b or A21-15, using an amount of virus (TCID$_{50}$ units) to give the appropriate virus:cell ratio. All infections were performed in quadruplicate. The cells were harvested 11 days p.i., and the polyhedra were isolated and quantified. The results of this experiment, shown in FIG. 1A and FIG. 1B, demonstrated that isolate 122b is able to establish successful polyhedra production ($\geq 1 \times 10^8$ polyhedra produced per flask) in cells infected at virus:cell ratios of from 1:1 to 1:500. In contrast, isolate A21-15 exhibited successful polyhedra production only in cells infected at virus:cell ratios of 1:1, 1:5, and 1:10. The values shown in FIG. 1A and FIG. 1B are the averages of four determinations±one standard deviation.

An analysis of the data presented in FIG. 1A and FIG. 1B shows that polyhedra production by cells infected with isolate 122b was significantly higher than polyhedra production by cells infected with isolate A21-15. At virus:cell ratios of from 1:1 to 1:100, isolate 122b infections resulted in from 1.9 to 4.5 times greater polyhedra production than A21-15-infected cells. Statistical analysis of data was performed using the StatView program from Abacus Concepts (Berkeley, Calif.). These results demonstrate that isolate 122b could generate successful polyhedra production in cells infected with far fewer virus particles than wild-type virus. Consequently, production of isolate 122b would require fewer scale-up steps, and hence would be less costly to produce.

Analysis of Budded Virus (BV) Production by Isolate 122b

The amount of BV released by cells infected by isolate 122b was determined and compared to the amount of BV released by cells infected with A21-MPV, an isolate that produces budded virus at levels comparable to wild-type virus, and to the LdNPV FP isolates A21-2, B21-1, 122-2, 163-2, and 5–6 (Slavicek, et al., *Biol. Con.* 5:251–261, 1995; Bischoff and Slavicek, *J. of Virology* 71:1097–1106, 1997). Viral isolates of 122b, A21-MPV, A21-2, B21-1, 122-2, 163-2, and 5–6 were used to infect Ld652Y cells, in triplicate, at ten TCID$_{50}$ units per cell in T25 flasks seeded with $1 \times 10^6$ cells. Seven days p.i., the medium containing BV was harvested, and the amount of BV present was determined by the end-point dilution assay. Ld652Y cells ($1 \times 10^4$ per well) were seeded in P96 plates and allowed to attach for one hour. The cells were infected with virus at $10^{-1}$ to $10^{-11}$ dilutions and the plates were incubated at 27° C. Two weeks p.i., the plates were scored, and the viral titer was expressed as the $TCID_{50}$ per ml of cell culture medium (FIGS. 2A and 2B). The LdNPV isolate 122b produced significantly more BV than isolate A21-MPV. (ANOVA, Fisher's PLSD, P<0.05). There was no significant difference between the amounts of BV produced by isolate 122b and the LdNPV FP mutants (isolates A21-2, B21-1, 122-2, 163-2, and 5–6). The values given in FIGS. 2A and 2B are the averages of three determinations± one standard deviation. Statistical analysis of data was performed using the StatView program from Abacus Concepts (Berkeley, Calif.).

Stability of polyhedra production by 122b-infected cells

The formation of FP mutants during serial passage of LdNPV-infected cells in cell culture is a significant impediment to development of cell culture virus production systems that must be resolved before LdNPV can be commercially produced in bioreactors. As a consequence of the FP mutant problem, only LdNPV isolates that are resistant to FP mutant formation have been successfully produced in bioreactors (Slavicek, et al., *J. Invert. Path.* 67:153–160, 1996; personal communication, The American Cyanamid Company).

The stability of the many polyhedra phenotype of isolate 122b was assessed and compared to the stability of wild-type LdNPV isolates through serial passage. Plaque-purified lines of LdNPV isolates A21, B21, 122, 163, and isolates 122b and A21-MPV were serially passaged in the Ld652Y cell line. The passage study was initiated by infecting Ld652Y cells, plated at a density of $2 \times 10^5$ /ml, with 0.1 $TCID_{50}$ unit per cell. The $TCID_{50}$ value and the number of polyhedra produced per flask after each serial passage was determined as described above. BV from the first passage was used as inoculum for the second culture. Each subsequent passage was performed similarly. Serial passage was discontinued after the isolates had become predominantly FP, as indicated by a reduction in the number of polyhedra per flask, with a concomitant increase in the number of BV produced.

Figure 4:
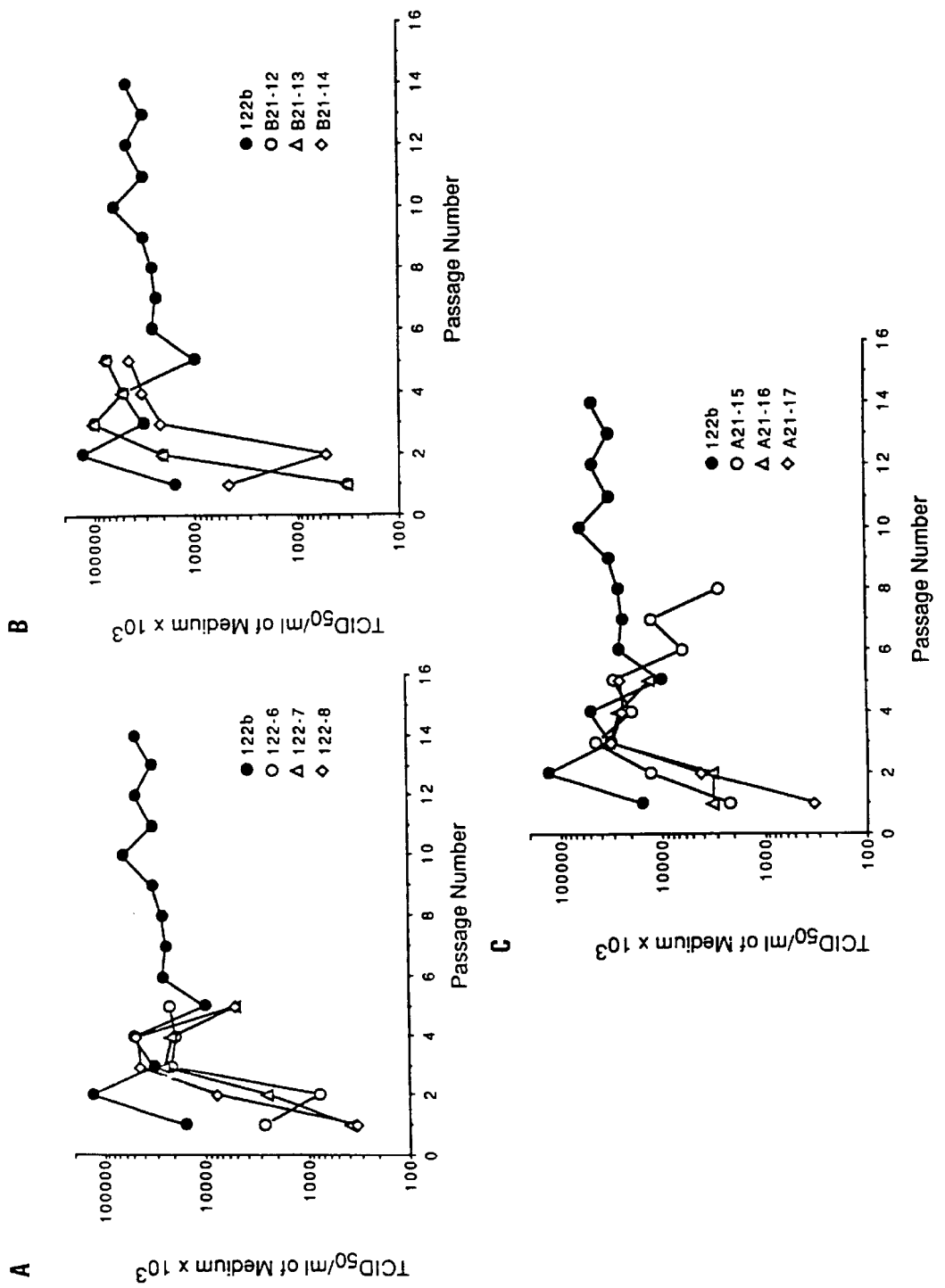
FIG. 4 is a graphical representation of the numbers of budded virus produced in cells infected with the indicated LdNPV isolates through fourteen transfers.

The stability of polyhedra production and budded virus production in cells infected with various LdNPV isolates are shown in FIG. 3 and FIG. 4, respectively. Viral isolate 122b exhibited stable polyhedra and budded virus production after 14 serial passages, whereas all plaque purified lines of LdNPV isolates A21, B21, 122, and 163 formed FP mutants. The FP mutants became the predominate virus type after a few serial passages as indicated by the decrease in polyhedra formation (FIG. 3) and increase in BV production (FIG. 4). These results demonstrate that FP mutants do not become the predominate virus type during serial passage of isolate 122b. FP mutants of isolate 122b do form; however, the number of BV produced by 122b FP mutants (e.g., 122b12f) is comparable to the number of BV produced by isolate 122b (Table 1). Consequently, FP mutants do not become the predominate virus type during serial passage of isolate 122b.

TABLE 1

| Viral Isolate | $TCID_{50}$/ml Medium + SD |
| --- | --- |
| 122b | $3.6 \times 10^7 \pm 1.5 \times 10^7$ |
| 122b12f | $3.4 \times 10^7 \pm 8.5 \times 10^6$ |

Figure 5:
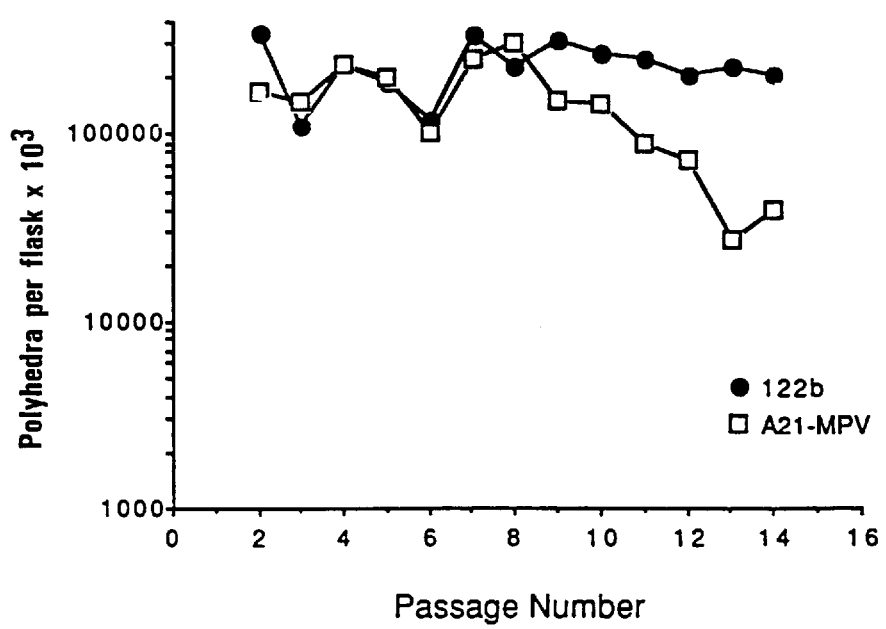
FIG. 5 is a graphical representation of the number of polyhedra produced in cells infected with LdNPV isolates as a function of the number of serial passages.

Comparison of polyhedra production by isolates 122b and A21-MPV during serial passage LdNPV isolate A21-MPV exhibits enhanced polyhedra production stability during serial passage (Slavicek, et al., *J. Invertebr. Pathol.* 67:153–160, 1996; Slavicek, et al., U.S. Pat. No. 5,420,031). The stability of polyhedra formation exhibited by isolates 122b and A21-MPV were compared by examining polyhedra production as a function of serial passage. Serial passage was performed as described in the preceding section. After approximately 10 serial passages, the number of polyhedra produced by isolate A21-MPV began to decrease, whereas polyhedra production by isolate 122b remained essentially constant through 14th serial passages (FIG. 5). After the 14th serial passage, approximately 70% of the A21-MPV virus exhibited an FP phenotype; in contrast, there was no evidence of FP mutant formation in isolate 122b after the 14th serial passage. These results demonstrate that isolate 122b exhibits greater polyhedra production stability during serial passage than isolate A21-MPV.

Restriction endonuclease analysis of isolates 122 and 122b

Genomic DNA from budded virus of LdNPV isolates 122 and 122b were examined for restriction fragment length polymorphisms. The budded virus present in medium in which infected cells were grown were pelleted by centrifugation at 112,700×g for 45 minutes at 4° C. The pellet was resuspended overnight in 0.1×TE (0.01M Tris, pH 8.0, 1 mM EDTA, pH 8.0) at 4° C. Viral DNA was isolated as previously described (Slavicek, et al., *Biol. Cont.*, 5:251–261, 1995). Viral DNA was subjected to restriction endonuclease digestion using BglII, EcoRI, EcoRV, HindIII, BamHI, and PstI. The DNA fragments were separated by agarose gel electrophoresis and visualized following staining with ethidium bromide. There were no detectable differences in restriction fragment sizes between the two isolates. The approach used in this comparison will detect DNA insertions or deletions of approximately 0.5 kb or greater in length, and nucleotide addition, deletions, or alterations that create or eliminate restriction endonuclease recognition sites of the enzymes employed. These results indicate that isolate 122b is a mutant derivative of isolate 122.

Comparative bioassays using isolate 122b and GYPCHEK

Comparative bioassays were performed as described in Slavicek, et al. (*J. Invertebr. Pathol.*, 59:1242–148, 1992) using polyhedra from isolate 122b and a standard gypsy moth virus, GYPCHEK. GYPCHEK is the name of the LdNPV registered by the Forest Service that is currently in use for gypsy moth control. Briefly, polyhedra from isolate 122b that were produced in the Ld652Y cell line, were suspended in 10 ml sterile 0.05M Tris-HCl, pH 7.2, and briefly sonicated to disperse the polyhedra. A 100 mg lyophilized sample of GYPCHEK was similarly suspended and vigorously ground in a glass tissue homogenizer for three minutes. Five serial 10-fold dilutions of the 122b and the GYPCHEK virus suspensions were prepared using Tris buffer as the diluent. Dilutions were prepared such that final polyhedra concentrations in diet fed to test insects ranged between $1 \times 10^2$ and $1 \times 10^7$ polyhedra/ml. One milliliter of the diluted polyhedra sample was added to 99 ml of tempered (52° C.) diet and vigorously mixed with a variable speed stirrer (5000 rpm) for 30 seconds. Virus-treated diet was cooled and cut into 1.25 cm cubes.

Each virus dosage was presented to five groups of 10 newly molted second instar larvae from a standard laboratory strain of the gypsy moth (New Jersey). Each group of 10 larvae was confined to a 100×15 mm plastic petri plate and given two 1.25 cm virus-treated diet cubes on which to feed for a 48-hour period. Larvae were maintained in a growth chamber at 24±2° C. under a 16/8 hour light/dark photoperiod.

The larvae were observed daily for mortality. Dead larvae were removed and examined microscopically to confirm virus deaths. Mortality data were examined by Probit analysis using a POLO-PC program (LeOra Software, Berkeley, Calif.). Potency of isolate 122b relative to standard GYPCHEK was examined by comparing LC50 values. The results of the bioassay are shown in Table 2. These results suggest that polyhedra of isolate 122b produced in cell culture are less potent than GYPCHEK, which contains polyhedra produced in gypsy moth larvae. However, the limits of isolate 122b and GYPCHEK overlapped, which indicates that the difference in potency between these two viral preparations is not significant.

TABLE 2

| Isolate | LC-50[a] | Limits[b] |
|---------|----------|-----------|
| 122b    | 15,194   | 7405–32,546 |
| GYPCHEK | 9040     | 6159–13,324 |

[a]LC-50 (lethal concentrations) values are the number of polyhedra per ml of diet that cause 50% larval mortality.
[b]Limit values are numbers of polyhedra per ml of diet that cause 50% larval mortality.

Proposed Viral Formulation and Application for Gypsy Moth Control

We envision that the 122b isolate may be applied to insects or insect habitats in a manner similar to that currently used in LdNPV applications. The mode of infection is through ingestion of the virus by the insect. Insects may become infected as a consequence of ingestion of virus present on the insect or on insect egg masses. For treatment of plants, treating the leaf surfaces with the viral insecticide is an effective application mode.

LdNPV has been formulated for control of gypsy moth as described below:
- 10 g GYPCHEK ($5.0 \times 10^{10}$ polyhedra/g)
- 227 g (6% w/v) Orzan La. (a sunscreen, ITT Taynonier, Seattle, Wash.)
- 0.47 l (12.5% by volume) Pro Mo liquid supplement (Southern States Cooperative, Richmond, Va.).
- 77.6 ml (2% by vol) Rhoplex B60A (a sticker-spreader, Rohm & Haas Company, Philadelphia, Pa.)
- 3.24 l (88.5% by vol) water We envision that an effective viral insecticide can be similarly prepared using polyhedra of isolate 122b.

We claim:

1. A gypsy moth viral isolate having the characteristics of ATCC VR2577, wherein said characteristics include the ability to establish successful infection of cultured cells at a low multiplicity of infection, enhanced polyhedra production, enhanced budded virus production, and stable polyhedra production during serial passage.

2. A preparation of gypsy moth virus designated ATCC VR2577, deposited at the American Type Culture Collection.

3. The viral isolate of claim 1, wherein polyhedra production in cultured cells infected with the viral isolate at a virus:cell ratio of from 1:1 to 1:100, is at least 2.5 times greater than that in cultured cells infected with a wild-type isolate.

4. The viral isolate of claim 1, wherein polyhedra production in cultured cells infected with the viral isolate at a virus:cell ratio of from 1:1 to 1:100 is at least 3.5 times greater than that in cultured cells infected with a wild-type isolate.

5. The viral isolate of claim 1, wherein polyhedra production in cultured cells infected with the viral isolate at a virus:cell ratio of from 1:1 to 1:100 is at least 4.5 times greater than that in cultured cells infected with a wild-type isolate.

6. The viral isolate of claim 1, wherein the viral isolate is able to establish successful infection of cultured cells at virus:cell ratios of less than 1:10.

7. The viral isolate of claim 1, wherein the viral isolate is able to establish successful infection of cultured cells at virus:cell ratios of less than 1:100.

8. The viral isolate of claim 1, wherein the viral isolate is able to establish successful infection of cultured cells at virus:cell ratios of 1:500.

9. The viral isolate of claim 1, wherein the amount of budded virus produced in cells infected with the viral isolate is at least 5 times greater than the number of budded virus produced in cells infected with viral isolate ATCC VR2396.

10. The viral isolate of claim 1, wherein the viral isolate exhibits stable polyhedra production after more than 10 serial passages.

11. The viral isolate of claim 1, wherein the viral isolate exhibits stable polyhedra production after more than 14 serial passages.

12. The viral isolate of claim 1, wherein the viral isolate is propagated in cell culture using the *L. dispar* 652Y (Ld652Y) ovarian cell line.

13. An insecticidal composition comprising an insecticidally effective amount of polyhedra of the virus of claim 1 and an inert carrier.

14. The insecticidal composition of claim 13, wherein the concentration of polyhedra is at least about $1 \times 10^8$/liter.

15. The insecticidal composition of claim 13, wherein the concentration of polyhedra is at least about $1 \times 10^9$/liter.

16. The insecticidal composition of claim 13, wherein the concentration of polyhedra is at least about $1 \times 10^{10}$/liter.

17. The insecticidal composition of claim 9, wherein the concentration of polyhedra is about $1 \times 10^{11}$/liter.

18. A method of protecting plants from insects against which LdNPV is toxic, said method comprising applying to such insects or insect habitat an insecticidally effective amount of the virus of claim 1.

19. The method of claim 18, wherein the virus is formulated as the insecticidal composition of claim 13.

20. The method of claim 18, additionally comprising the step of applying a second insecticidally effective amount of a second insecticidal virus.

* * * * *